United States Patent
Min et al.

(10) Patent No.: US 11,941,839 B2
(45) Date of Patent: Mar. 26, 2024

(54) 10-20 SYSTEM-BASED POSITION INFORMATION PROVIDING METHOD

(71) Applicant: NEUROPHET Inc., Seoul (KR)

(72) Inventors: Dae Gyu Min, Incheon (KR); Jun Kil Been, Seoul (KR); Dong Hyeon Kim, Seoul (KR)

(73) Assignee: NEUROPHET Inc., Seoul (KR)

( * ) Notice: Subject to any disclaimer, the term of this patent is extended or adjusted under 35 U.S.C. 154(b) by 370 days.

(21) Appl. No.: 17/384,025

(22) Filed: Jul. 23, 2021

(65) Prior Publication Data
US 2021/0350571 A1  Nov. 11, 2021

Related U.S. Application Data

(63) Continuation of application No. PCT/KR2019/016113, filed on Nov. 22, 2019.

(30) Foreign Application Priority Data

Jan. 31, 2019  (KR) .................. 10-2019-0012493

(51) Int. Cl.
*G06T 7/73* (2017.01)
*A61B 5/00* (2006.01)

(52) U.S. Cl.
CPC .............. *G06T 7/73* (2017.01); *A61B 5/684* (2013.01); *G06T 2207/30016* (2013.01)

(58) Field of Classification Search
CPC .. G06T 7/73; G06T 2207/30016; A61B 5/684
See application file for complete search history.

(56) References Cited

U.S. PATENT DOCUMENTS

| | | | |
|---|---|---|---|
| 2012/0265261 A1 | 10/2012 | Bikson et al. | |
| 2014/0249385 A1* | 9/2014 | Wada | A61B 5/291 600/383 |
| 2017/0120041 A1* | 5/2017 | Wenger | A61B 5/05 |

FOREIGN PATENT DOCUMENTS

| | | | | |
|---|---|---|---|---|
| JP | 2007-185491 A | | 7/2007 | |
| JP | 2007185491 A | * | 7/2007 | ............. A61B 10/00 |
| JP | 2011-517962 A | | 6/2011 | |
| JP | 2018-174962 A | | 11/2018 | |
| KR | 10-1428624 B1 | | 9/2014 | |
| KR | 10-1797375 B1 | | 12/2017 | |

OTHER PUBLICATIONS

International Search Report issued in PCT/KR2019/016113; dated Mar. 3, 2020.

(Continued)

*Primary Examiner* — John J Lee
(74) *Attorney, Agent, or Firm* — Studebaker & Brackett PC

(57) ABSTRACT

Provided is a 10-20 system-based position information providing method performed by a computer. The method comprises the steps of: obtaining a head image of a subject; receiving, from a user, an input of at least four reference points on the basis of the head image; calculating central coordinates in the head image on the basis of the at least four reference points; and providing 10-20 system-based position information on the basis of the central coordinates.

13 Claims, 11 Drawing Sheets

(56) References Cited

OTHER PUBLICATIONS

An Office Action; "Notice of Reasons for Refusal," mailed by the Japanese Patent Office dated Jul. 26, 2022, which corresponds to Japanese Patent Application No. 2021-544407 and is related to U.S. Appl. No. 17/384,025.
Communication pursuant to Rule 164(1) EPC issued by the European Patent Office dated Oct. 12, 2022, which corresponds to European Patent Application No. 19913173.1-1210 and is related to U.S. Appl. No. 17/384,025.
Krings T. et al., "Accuracy of EEG dipole source localization using implanted sources in the human brain", Clinical Neurophysiology, Elsevier, Amsterdam, NL, vol. 110, No. 1, Jan. 1, 1999, pp. 106-114, XP027401342.
Meyer B.-U. et al., "Coil placement in magnetic brain stimulation related to skull and brain anatomy", Electroencephalography and Clinical Neurophysiology/Evoked Potentials Section, Elsevier, vol. 81, No. 1, Feb. 1, 1991, pp. 38-46, XP024335497, doi: 10.1016/0168-5597(91)90102-4.
Chapman R. M. et al., "Selective localization of alpha brain activity with neuromagnetic measurements", Electroencephalography and Clinical Neurophysiology, Elsevier, NL, vol. 58, No. 6, Dec. 1, 1984, pp. 569-572, XP024287486, doi: 10.1016/0013-4694(84)90047-6.
Ueno S. et al, "Vectorial Properties in Functional Mapping of The Human Brain Obtained by Vectorial Magnetic Stimulation", New Frontiers of Biomedical Engineering—Innovations From Nuclear to Space Technology: 13th Annual International Conference of the IEEE Engineering in Medicine and Biology Society: Oct. 31-Nov. 3, 1991, Orlando, FL, USA; Proceedings, Oct. 31, 1991, pp. 855-856, XP010101732.
Summons to attend oral proceedings pursuant to Rule 115(1) EPC issued by the European Patent Office on Dec. 1, 2023, which corresponds to European Patent Application No. 19913173.1-1210 and is related to U.S. Appl. No. 17/384,025.
Anonymous: 10-20 system (EEG)—Wikipedia, Dec. 12, 2018, XP093102683, Retrieved from the Internet: URL: https://en.wikipedia.org/w/index.php?title=10-20_system_(EEG)&oldid=873391176, total 4 pages.
Polking John C., "Mapping the sphere", May 7, 1998, XP093105251, https://math.rice.edu/~polking/cartography/ Retrieved from the Internet: URL:https://web.archive.org/web/19980507045623/https://math.rice.edu/~polking/cartography/cart.pdf, total 30 pages.

* cited by examiner

10-20 SYSTEM-BASED POSITION INFORMATION PROVIDING METHOD

CROSS-REFERENCE TO RELATED APPLICATIONS

The present application is a continuation of International Patent Application No. PCT/KR2019/016113, filed on Nov. 22, 2019, which is based upon and claims the benefit of priority to Korean Patent Application No. 10-2019-0012493 filed on Jan. 31, 2019. The disclosures of the above-listed applications are hereby incorporated by reference herein in their entirety.

BACKGROUND

Embodiments of the present invention described herein relate to a method for providing position information based on the 10-20 system.

An electrical brain stimulation manner refers to a manner of attaching electrodes to an inner portion or an outer portion of a head to allow a current to flow, such that the current is finally applied to a brain. The electrical brain stimulation manner, which is a non-invasive treatment manner for simple operation, has been extensively used to treat various brain diseases depending on positions, to which the stimulation is applied, and the type of the stimulation.

In addition, even an electroencephalogram (EEG) manner to measure electricity activity resulting from brain activity of an object has been extensively used in neurology and neuropsychiatric treatment.

The electrical brain stimulation manner and the EEG manner are both non-invasive tests and treatment manners, and have the advantage of simple operation. However, since persons are different from each other in brain structure and head shape, a doctor may not attach a patch to an exact position for an operation. Accordingly, there is required a method of attaching a patch to an exact position by reflecting mutually different brain shapes of persons.

SUMMARY

Embodiments of the present invention provide a method for providing position information based on a 10-20 system.

The objects of the present invention are not limited to the above, but other effects, which are not mentioned, will be apparently understood to those skilled in the art.

According to an embodiment of the present invention, a method for providing position information based on a 10-20 system, which is performed by a computer, includes obtaining a head image of an object, receiving, from a user, at least four reference points based on the head image, calculating central coordinates of the head image based on the at least four reference points, and providing the position information based on the 10-20 system, based on the central coordinates.

According to an embodiment of the present invention, the receiving of the at least four reference points may include receiving front, rear, left, or right reference points of a head, which are included in the head image.

According to an embodiment of the present invention, the calculating of the central coordinates of the head image may include calculating a point at which the front, rear, left, or right reference points of the head cross each other, as the central coordinates.

According to an embodiment of the present invention, the providing of the position information based on the 10-20 system may include deriving a coordinate system of the 10-20 system by using distance information on a first connection line, which is obtained by linking the front and back reference points of the head with each other based on the central coordinates, and distance information on a second connection line which is obtained by linking the left and right reference points of the head to each other based on the central coordinates.

According to an embodiment of the present invention, the method may further include setting a position of an electrode, which is to be attached to the head of the object, on the head image, and the providing of the position information based on the 10-20 system may include providing information on the set position of the electrode based on the central coordinates of the 10-20 system, and calculating the position information of the electrode based on the first point extending from a point, at which the electrode is positioned, and positioned on the first connection line or a second point extending from the point, at which the electrode is positioned, and positioned on the second connection line.

According to an embodiment of the present invention, the calculating of the position information of the electrode may include deriving a first distance of the electrode, based on a geodesic line between the central coordinates and the first point, deriving a second distance of the electrode, based on a geodesic line between the first point and the point at which the electrode is positioned, and calculating the position information of the electrode on the central coordinates of the 10-20 system, based on the first distance of the electrode and the second distance of the electrode.

According to an embodiment of the present invention, the calculating of the position information of the electrode may include deriving a first distance of the electrode, based on a geodesic line between the central coordinates and the second point, deriving a second distance of the electrode, based on a geodesic line between the second point and the point at which the electrode is positioned, and calculating the position information of the electrode on the central coordinates of the 10-20 system, based on the first distance of the electrode and the second distance of the electrode.

According to an embodiment of the present invention, the method further include providing information on an optimal stimulation position, to which an electrical stimulation is applied, of the head of the object, based on the position information of the 10-20 system.

According to an embodiment of the present invention, the providing of the information on the optimal stimulation position may include simulating stimulation results for a plurality of stimulation positions, based on the plurality of stimulation positions provided by the 10-20 system, deriving the linear relationship between the plurality of stimulation positions by using the simulated stimulation results, and providing the information on the optimal stimulation position based on the linear relationship.

According to an embodiment of the present invention, the simulating of the stimulation results for the plurality of stimulation positions may include setting one reference stimulation position of the plurality of stimulation positions, and acquiring a stimulation result for a stimulation pair between the reference stimulation position and each of different stimulation positions of the plurality of stimulation positions other than the reference stimulation position.

According to an embodiment of the present invention, the deriving of the linear relationship between the plurality of stimulation positions may include driving the linear relationship between electric fields, which are output as a specific stimulation is applied under a specific stimulation condition, from the stimulation result for the stimulation pair.

According to an embodiment of the present invention, the providing of the information on the position of the optimal stimulation may include providing the information on the position of the optimal stimulation under a desired stimulation condition, based on the linear relationship.

According to an embodiment of the present invention, a computer program is linked to a computer, which is hardware, and stored in a recording medium readable by the computer such that the method for providing position information based on the 10-20 system is performed.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
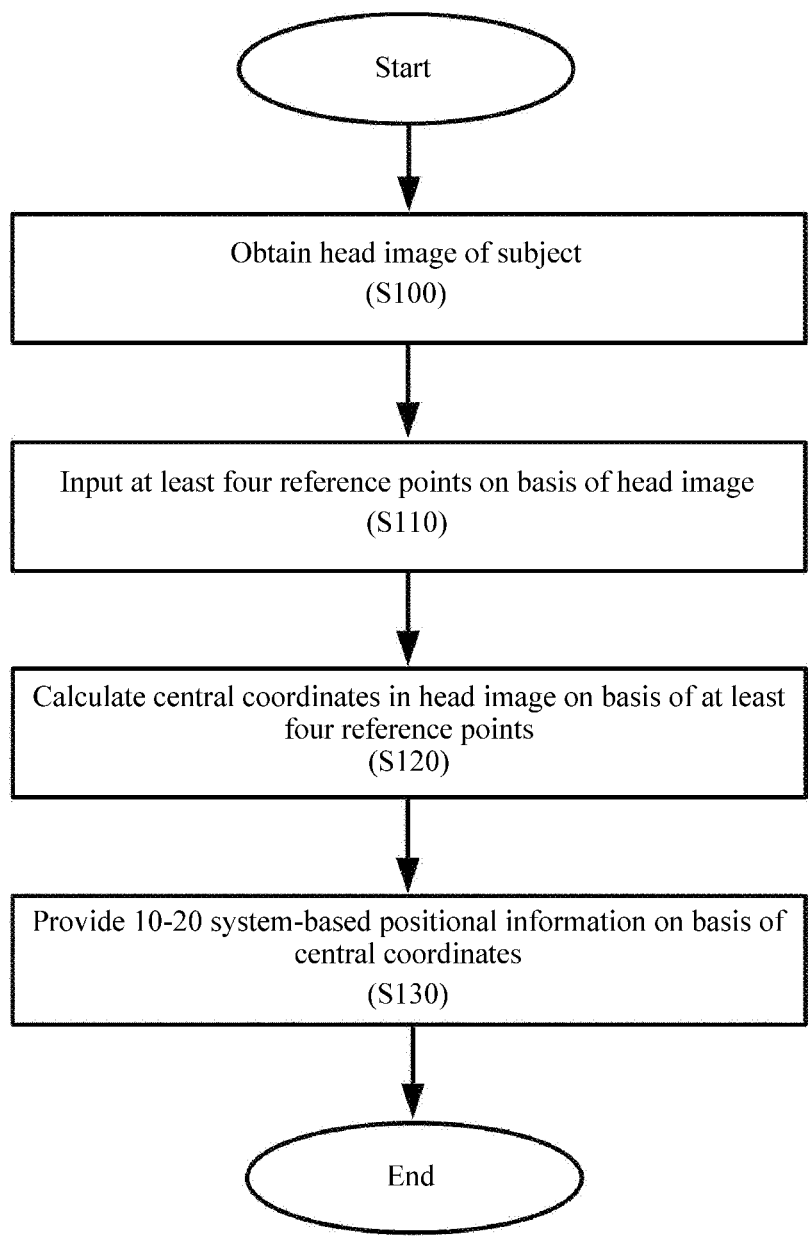
FIG. 1 is a flowchart illustrating a method for providing position information based on a 10-20 system, according to an embodiment of the present invention.

Advantage points and features of the present invention and a method of accomplishing thereof will become apparent from the following description with reference to the following figures, wherein embodiments will be described in detail with reference to the accompanying drawings. However, the present invention may be embodied in various different forms, and should not be construed as being limited only to the illustrated embodiments. Rather, these embodiments are provided as examples so that the present invention will be thorough and complete, and will allow those skilled in the art to fully understand the scope of the present invention. The present invention may be defined by scope of the claims.

The terminology used herein is provided for explaining embodiments, but the present invention is not limited thereto. As used herein, the singular terms "a," "an" and "the" are intended to include the plural forms as well, unless the context clearly indicates otherwise. Furthermore, it will be further understood that the terms "comprises", "comprising," "includes" and/or "including", when used herein, specify the presence of stated elements, steps, operations, and/or devices, but do not preclude the presence or addition of one or more other components, steps, operations and/or devices. The same reference numerals will be assigned to the same component throughout the whole specification, and "and/or" refers to that components described include not only individual components, but at least one combination of the components. It will be understood that, although the terms "first", "second", etc., may be used herein to describe various components, these components should not be limited by these terms. These terms are only used to distinguish one component from another component. Thus, a first component to be described below may be a second component without departing from the teachings of the present invention.

Unless otherwise defined, all terms (including technical and scientific terms) used herein have the same meaning as commonly understood by those skilled in the art. It will be further understood that terms, such as those defined in commonly used dictionaries, should be interpreted as having a meaning that is consistent with their meaning in the context of the relevant art and will not be interpreted in an idealized or overly formal sense unless expressly so defined herein Hereinafter, exemplary embodiments of the present invention will be described with reference to accompanying drawings.

FIG. 1 is a flowchart illustrating a method for providing position information based on a 10-20 system, according to an embodiment of the present invention.

The method illustrated in FIG. 1 includes steps performed by a computer in time-series. In the present specification, the meaning of a computer may cover the meaning of a computing device including at least one processor.

Referring to FIG. 1, the computer may acquire two images of an object (S100).

In this case, the object may include a human being, an animal, a part of the human being, or a part of the animal.

A head image refers to a medical image obtained by photographing a head including a brain of an object. For example, a computed tomography (CT) image, a magnetic resonance imaging (MRI) image, or a positron emission tomography (PET) image, which is captured by medical imaging equipment, may be included.

Figure 2:
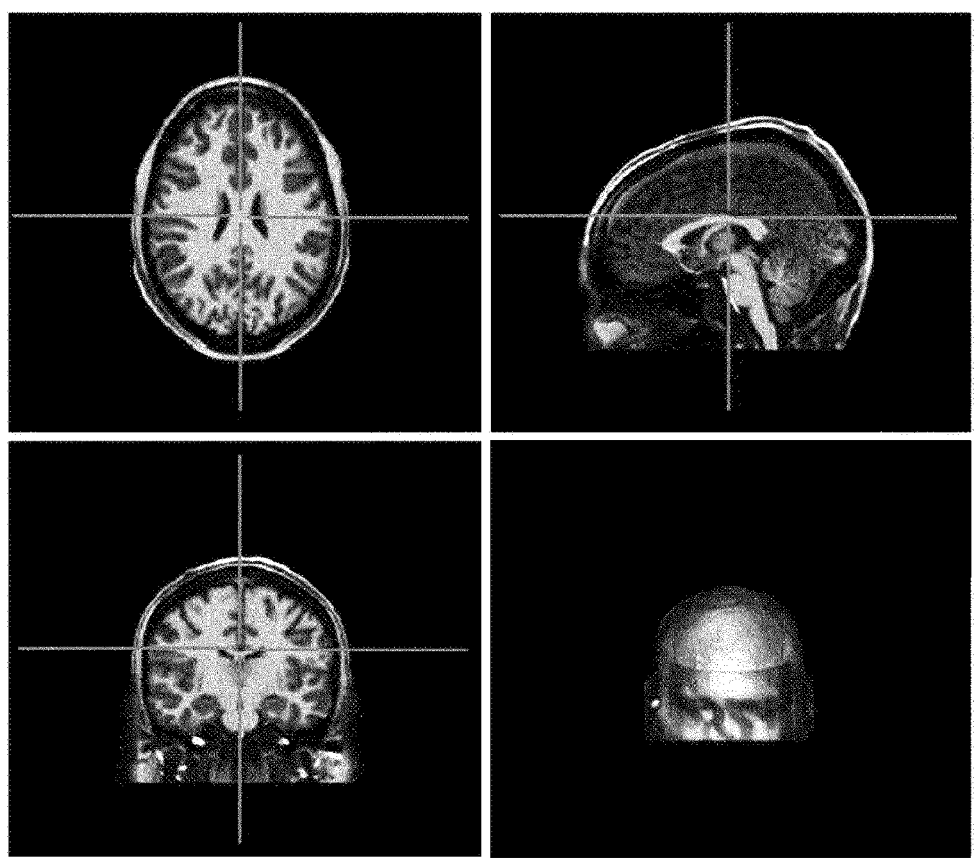
FIG. 2 is a view illustrating a head image of an object, according to an embodiment of the present invention.

According to an embodiment, the computer may acquire a head image of the object, such as the CT, the MRI, or the PET, of the object, and may perform three-dimensional rendering based on the acquired head image to generate a 3D modeled head image. The computer may display the 3D modeled head image in an axial, sagittal, or coronal direction. For example, FIG. 2 is a view illustrating a head image of an object, according to an embodiment of the present invention.

The computer may receive at least four reference points based on the head image from the user (S110).

Figure 3:
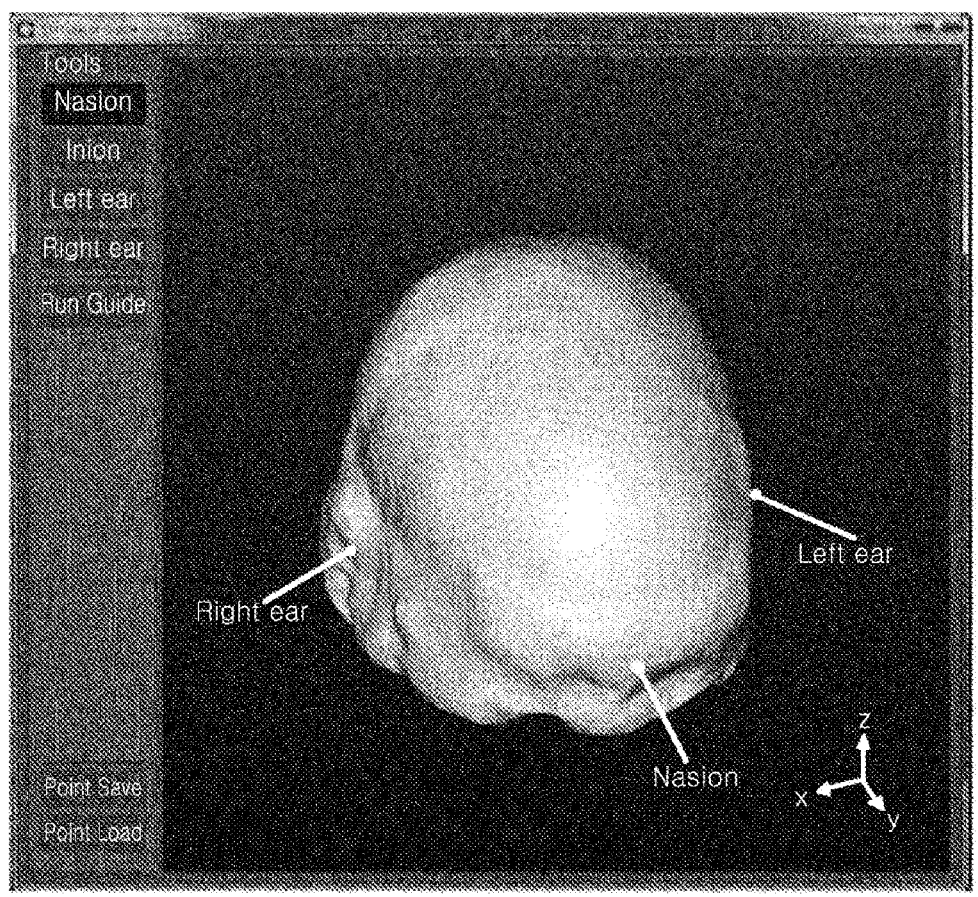
FIG. 3 illustrates results obtained as a user sets four reference points (e.g., Nasion, Inion, Left ear, Right ear) on a head image, according to an embodiment of the present invention.

According to an embodiment, the computer may receive, from the user, reference points, which corresponds to the front, back, left, and right of the head, on the head image displayed on the screen. For example, the front reference point on the head is Nasion, the back reference point on the head is inion, the left reference point on the head is the left ear, and the right reference point on the head is the right ear. For example, FIG. 3 illustrates results obtained as the user sets four reference points (e.g., Nasion, Inion, Left ear, Right ear) on the head image.

The computer may calculate the central coordinates on the head image, based on at least four reference points (S120).

According to an embodiment, the computer may calculate a point at which the front, back, left, and right reference points, which are received from the user, of the head image, cross each other, as the central coordinates.

The computer may provide 10-20 system-based position information based on the central coordinates (S130).

According to an embodiment, the computer may derive a coordinate system of the 10-20 system by using the distance information on a first connection line, which is obtained by linking the front and back reference points of the head with each other based on the central coordinates, and the distance information on a second connection line which is obtained by linking the left and right reference points of the head to each other based on the central coordinates. For example, the computer may derive the coordinate system of the 10-20 system by dividing the first connection line by 10% or 20% of the whole distance of the first connection line from the central coordinates, and dividing the second connection line by 10% or 20% of the whole distance of the second connection line from the central coordinates.

Figure 4:
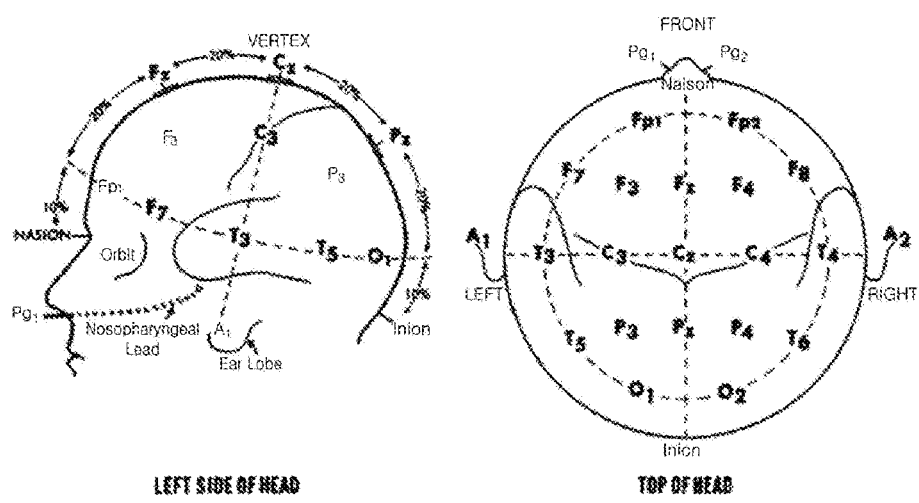
FIG. 4 is a view illustrating a 10-20 system derived, according to an embodiment of the present invention.

FIG. 4 is a view illustrating the 10-20 system derived, according to an embodiment of the present invention.

Referring to FIG. 4, the computer sets, as the central coordinates "Cz", the crossing point between the first connection line and the second connection line formed based on four front, back, left, and right reference points. Thereafter, the computer, which divides the first connection line and the second connection line from the central coordinates "Cz", divides each of the first connection line and the second connection line such that the distance (that is, the distance between two adjacent points) between division points positioned on each of the first connection line and the second connection line becomes 10% or 20% of each of the whole distance of the first connection line and the whole distance of the second connection line, and forms a concentric circle by connecting the division points about the central coordinates "Cz". In addition, the length of the concentric circle is measured and the concentric circle is divided such that each point is positioned at 10% or 20% of the distance. The computer may derive the coordinate system of the 10-20 system as illustrated in FIG. 4 at the final stage.

According to the present invention, as described above, as the coordinate system based on the 10-20 system is derived, the position for placing an electrode on the head image of the object may be effectively detected.

According to an embodiment of the present invention, the computer may set the position of the electrode to be attached to the head (that is, a scalp surface) of the object by using the head image, and may provide the information on the set position of the electrode, based on the coordinate system of the 10-20 system.

Figure 5:
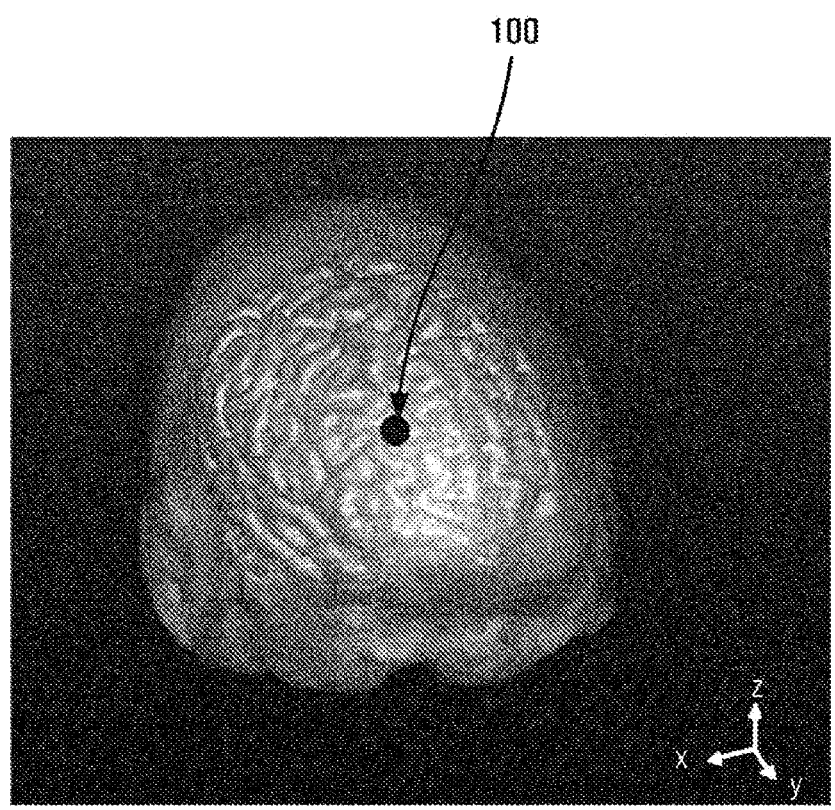
FIG. 5 is a view illustrating that a position of an electrode is set on a head image, according to an embodiment of the present invention.

For example, the computer may display the head image of the object through the screen, and may receive, from the user, the position of the electrode to be attached to the head of the object, through the displayed head image. Alternatively, the computer may display, on the head image, the position of the electrode determined based on clinical or theoretical grounds depending on the disease of the object, and may set, as the position of the electrode, a result from the simulation for obtaining the optimal position of the electrode to be attached to the object. For example, FIG. 5 is a view illustrating that the point 100 of the electrode on the head image is set, according to an embodiment of the present invention.

Thereafter, the computer may calculate set position information (that is, coordinate information) of the electrode from the coordinate system of the 10-20 system derived in step S100 to S130. According to an embodiment, the computer may calculate the position information based on the first point extending from a set point, at which the electrode is positioned, and positioned on the first connection line (that is, the line obtained by linking the front and rear reference points of the head) or a second point extending from the set point, at which the electrode is positioned, and positioned on the second connection line (that is, the line obtained by linking the left and right reference points of the head).

Figure 6:
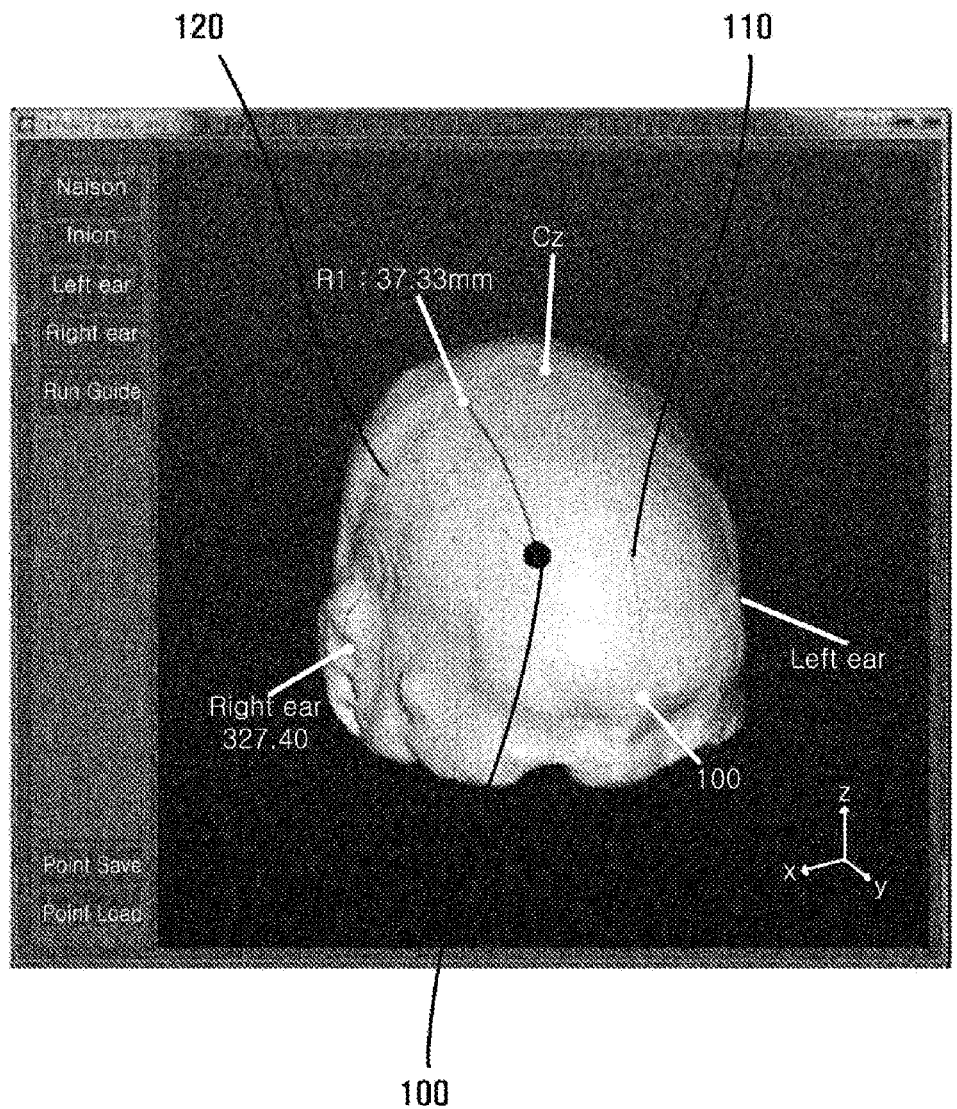
FIG. 6 is a view illustrating a procedure of calculating position information of an electrode, based on an 10-20 system, according to an embodiment of the present invention.

FIG. 6 is a view illustrating the procedure of calculating the position information of the electrode, based on the 10-20 system, according to an embodiment of the present invention.

Referring to FIG. 6, the computer may derive a first distance "D1" of the electrode, based on a geodesic line between the central coordinates "Cz" and the second point "R1".

In this case, the second point "R1" is a point extending from the point 100, at which an electrode is positioned, and positioned on a second connection line 120. For example, a line is drawn from the point 100, at which the electrode is positioned, while being in parallel to a first connection line 110, and a point at which the line meets the second connection line 120, is referred to as a second point "R1".

The geodesic line, which refers to a curved line, which has the shortest distance, of curved lines linking two spatial points, refers to a line formed between the central coordinates "Cz" and the second point "R1" and having the shortest path of paths that are able to be generated along a head surface.

The computer may derive a second distance "D2" of the electrode, based on a geodesic line between the second point "R1" and the point 100 at which the electrode is positioned. For example, the computer may draw a geodesic line, which is parallel to the first connection line 110, from the second point "R1", and calculate the distance from the second point "R1" to the point 100, at which the electrode is positioned, on the geodesic line, as the second distance "D2".

The computer may calculate the position information on the point 100, at which the electrode is positioned, on the coordinate system of the 10-20 system, based on the first distance "D1" and the second distance "D2".

Although the above description has been made with reference to FIG. 6 regarding that the position of the electrode is calculated based on the second point positioned on the second connection line, the position of the electrode may be calculated based on the first point positioned on the first connection line in the manner similar to the above-manner According to an embodiment, the computer may derive the first distance of the electrode based on the geodesic line between the central coordinates "Cz" and the first point, and may derive the second distance of the electrode based on the geodesic line between the first point and the point at which the electrode is positioned. In addition, the computer may calculate the position information of the electrode on the coordinate system of the 10-20 system, based on the first distance and the second distance.

In addition, according to the present invention, as described above, the computer may calculate the position information of the electrode on the coordinate system of the 10-20 system and may display a guide image on the 10-20 system as illustrated in FIG. 4.

In addition, according to the present invention, as described above, the computer may provide position information of the optimal electrical stimulation to be applied to the head of the object by using the coordinate system of the 10-20 system. The details thereof will be described below.

Figure 7:
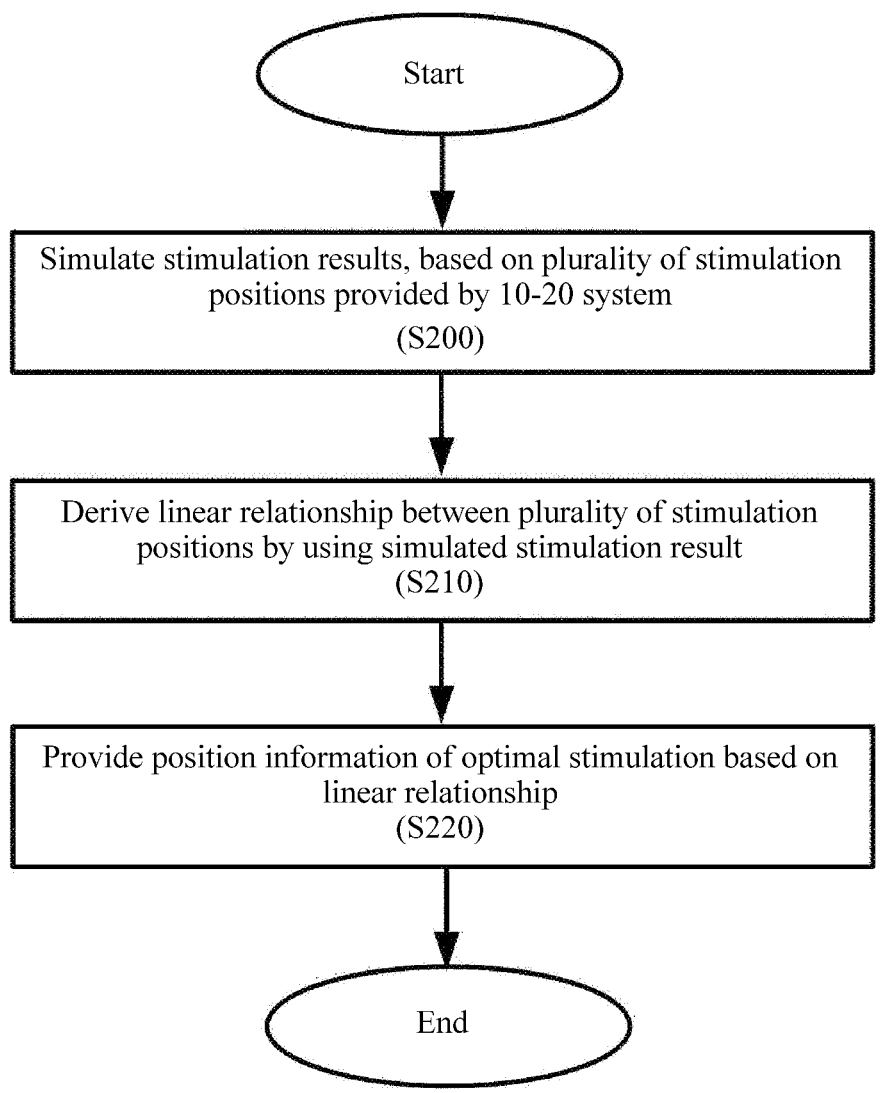
FIG. 7 is a flowchart illustrating a method for providing position information of the optimal stimulation based on a 10-20 system, according to an embodiment of the present invention.

FIG. 7 is a flowchart illustrating a method for providing position information of the optimal stimulation based on a 10-20 system, according to an embodiment of the present invention.

The method illustrated in FIG. 7 includes steps performed by a computer in time-series. In the present specification, the meaning of a computer may cover the meaning of a computing device including at least one processor.

First, the computer may derive the 10-20 system, based on step S100 to step S130 described in FIG. 1. In other words, the computer may perform step S200 to step S220 to be described below by using the 10-20 system derived based on the head image of the object.

Referring to FIG. 7, the computer may simulate stimulation results for a plurality of stimulation positions, based on the plurality of stimulation positions provided by the 10-20 system (S200).

According to a process of calculating the position of an electrode to apply the optimal stimulation in a conventional electrical brain stimulation method, a simulation is performed with respect to all combinations, which allow electrode pairs, for each of all positions, to which electrodes are attached, on the head of the object, such that an electrode pair for applying the optimal stimulation is acquired. In this case, since the calculation is performed with respect to all allowable combinations for each of all positions to which the electrodes are attached, on the head of the object, a computation amount and time to obtain the computation results are considerably required.

However, according to an embodiment of the present invention, the stimulation result may be simulated by using the stimulation position (that is, a position to which the electrode is to be attached) provided by the 10-20 system. According to an embodiment, the 10-20 system may perform simulation based on the number of preset stimulation positions (that is, positions to which electrodes are to be attached) based on the 10-20 system. For example, the number of preset stimulation positions may be set differently depending on 10-20 systems, and 16, 18, 32, 34, 64, 128, or 256 stimulation positions may be provided. Accordingly, the computer may perform the simulation based on the preset number of stimulation positions (16, 18, 32, 34, 64, 128, or 256 simulation positions) provided by the 10-20 system. In addition, according to an embodiment of the present invention, since a manner (which is to be described below) of simulating stimulation results with respect to the number of stimulation positions or less, which are provided by the 10-20 system is provided, the computation amount may be reduced such that the results may be rapidly obtained, which is different from the conventional manner of performing simulation with respect to all allowable combinations for each position.

According to an embodiment, the computer may set, as a reference stimulation position, one of a plurality of stimulation positions provided by the 10-20 system. Thereafter, the computer may fix the reference stimulation position, and may perform simulation while shifting remaining different stimulation positions of the plurality of stimulation positions other than the reference stimulation position, based on the fixed reference stimulation position. In other words, the computer may form a stimulation pair between each of the remaining different stimulation positions of the plurality of stimulation positions, which are provided by the 10-20 system, other than the reference stimulation position, and one reference stimulation position, and may perform a simulation for the stimulation pair to obtain a stimulation result.

Figure 8:
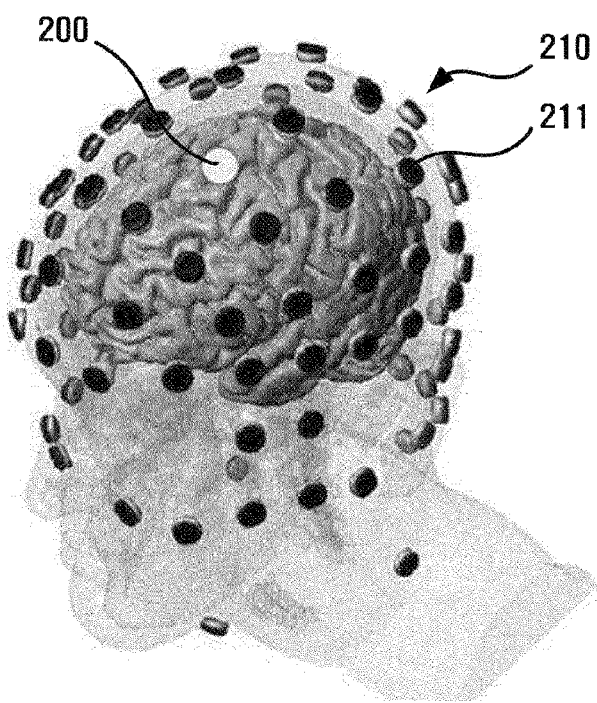
FIG. 8 is a view illustrating that stimulation results are simulated based on a plurality of stimulation positions provided by a 10-20 system, according to an embodiment of the present invention.

FIG. 8 is a view illustrating that stimulation results are simulated based on a plurality of stimulation positions provided by a 10-20 system, according to an embodiment of the present invention.

Referring to FIG. 8, the computer may calculate a coordinate system of the 10-20 system based on a head image of an object. For example, as illustrated in FIG. 8, the 10-20 system may be configured in the form of a coordinate system showing 120 stimulation positions. In this case, a reference stimulation position 200 is set from among the 120 stimulation positions, and a stimulation pair is formed between the set reference stimulation position 200 and each of remaining different stimulation positions 210 (that is, remaining positions of the 120 stimulation positions other than the reference stimulation position 200) to perform the simulation. For example, one stimulation position pair is formed between the reference stimulation position 200 and a first stimulation position 211 from among 119 remaining different stimulation positions 210, and the simulation may be performed with respect to the stimulation position pair, thereby calculating the stimulation result. In other words, the computer performs the simulation with respect to one reference stimulation position 200, and 119 stimulation positions paired with the reference stimulation position 200. In addition, simulation results for stimulation position pairs may be calculated by using the simulation results for the reference stimulation position 200 and 119 stimulation positions paired with the reference stimulation position 200. For example, when the reference stimulation position is the first stimulation position, stimulation results for stimulation pairs of a third stimulation position and a fifth stimulation position may be calculated by using each of a stimulation result for a stimulation pair between the first reference stimulation position and the third stimulation position and a stimulation result for a simulation pair between the first reference stimulation position and the fifth stimulation position. Accordingly, as illustrated in FIG. 8, when the coordinate system of the 10-20 system having 120 stimulation positions is used, the total 119 simulations are performed.

Referring back to FIG. 7, the computer may derive the linear relationship between the plurality of stimulation positions provided by the 10-20 system by using the simulated stimulation results obtained in step S200 (S210).

The stimulation result (for example, 119 stimulation results as illustrated in FIG. 8) obtained through the simulation has a linear characteristic. When the linear characteristic is used, a linear equation may be derived. For example, an electric field and a current density (for example, 119 stimulation results as illustrated in FIG. 8) resulting from the stimulation may have the linear relationship and may be expressed as in Equation 1.

$$E(C1_a, C2_b, C3_{-a-b}) = E(C1_a, C3_{-a}) + E(C2_b, C3_{-b}) \quad \text{Equation 1}$$

In this case, $E(C1_a, C2_b)$ represents current distribution of a brain when currents "a" and "b" are applied to electrodes "C1" and "C2", respectively.

When the linear relationship as in Equation 1 is used, a linear equation of the form Ax=b may be derived. In this case, x=(the amount of a current applied to the electrode) and b=(an electric field value, 1), in which a desired value of "b", that is, an electric field value, may be linearly obtained by adjusting "x".

The linear characteristic between the electric field and the current density as described above may be applied to calculating the position for the optimal stimulation. In this case, the optimal stimulation refers to a stimulation applied with the maximum efficiency under a condition (for example, an area for placing the electrode, or the output of the electrode) given with respect to a stimulation area which is suitable for a patient having a specific disease and obtained based on various clinical or theoretical studies. This may be similar to a manner of finding a solution of an inverse problem to find a condition for obtaining a desired result, instead of obtaining a result under the give condition, and may employ a numerical optimization manner. When interpreted "the applying of the stimulation with the maximum efficiency" as an actual electromagnetic meaning, the meaning of "the applying of the stimulation with the maximum efficiency" refers to a stimulation condition in which an electric field is maximized in a desired area. To obtain such a stimulation condition, a linear relationship may be derived from the results of simulation performed in step S200.

According to an embodiment, the computer may derive the linear relationship between electric fields, which are output as a specific stimulation is applied under a specific stimulation condition, from the stimulation result for each stimulation pair, which is obtained through the simulation performed in step S200. For example, the linear relationship may be expressed as in Equation 2. Equation 2 defines the relationship between a specific stimulation condition (m), and an electric field (E) output when applying a stimulation of $\propto$ times basic unit stimulation intensity (B).

$$E_m(r) = \alpha B_m(r) \quad \text{Equation 2}$$

E: electric field, r: coordinates inside the model, m: specific stimulation condition, α: ratio of actual stimulation to basic unit stimulation intensity, and B: basic unit stimulation intensity The electric field (E), which is obtained at the final stage in Equation 2, is equal to the product between the basic unit stimulation intensity (B) and the ratio (α) of the actual stimulation to the basic unit stimulation intensity. When the stimulation is applied with respect to the stimulation combination for various stimulation positions through such a manner, the linear relationship between two stimulations having different stimulation conditions may be expressed as in Equation 3.

$$E_{\sum m_1}(r) = \sum_{i=1}^{n} \alpha_i B_{m_i}(r) \quad \text{Equation 3}$$

$m_i$: $i^{th}$ simulation condition

The computer may derive a linear relationship between a combination of different stimulation conditions, and an electric field output when a stimulation is applied depending on the stimulation conditions, as in Equation 3. Accordingly, since the computer may find a solution of a linear simultaneously equation for various stimulation conditions and a desired stimulation intensity, the computer may obtain a stimulation condition for applying the maximum stimulation to a desired stimulation position through the numerical optimization manner. In this case, a least square method, a weighted least square method, or an L1 norm constrained method may be applied.

The computer may provide position information of the optimal stimulation based on the linear relationship derived in step S210 (S220).

According to an embodiment, since the computer may inversely find a desired result by obtaining a desired condition (for example, an electrode position, or an output of an electrode) for an electrical stimulation to be applied to the head of the object by using the linear relationship as in Equation 3, the computer may provide the optimal stimulation position, to which the electrical stimulation is applied, through the coordinate system of the 10-20 system.

Figure 9:
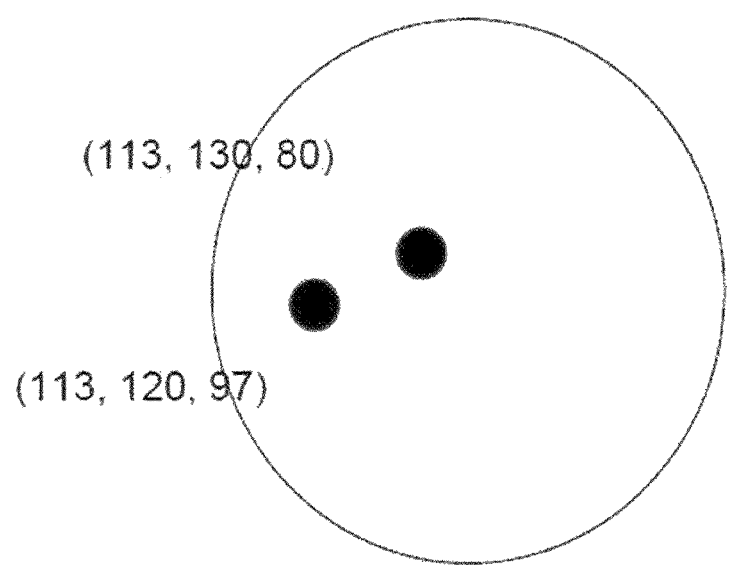
FIG. 9 is a view illustrating the optimal stimulation position through a conventional electrical brain stimulation manner.
Figure 10:
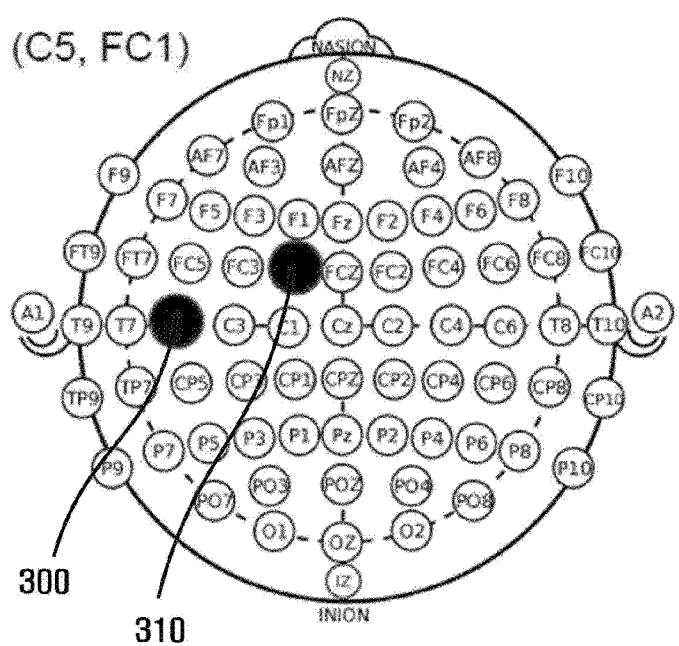
FIG. 10 is a view illustrating position information of the optimal stimulation, which is derived by using a coordinate system of a 10-20 system, according to an embodiment of the present invention.

FIG. 9 is a view illustrating the optimal stimulation position through a conventional electrical brain stimulation manner, and FIG. 10 is a view illustrating position information of the optimal stimulation, which is derived by using a coordinate system of a 10-20 system, according to an embodiment of the present invention.

Referring to FIG. 9, according to the conventional electrical brain stimulation manner, when providing an optimal stimulation position, a position pair of electrodes on the head of an object is simply displayed in the format of (x, y, z). Accordingly, since medical staffs, who attach electrodes to the object and perform a brain stimulation operation, attaches the electrode by using abstract positions of (x, y, z) on a head image, the medical staffs may not exactly detect the relevant position. Even if the electrodes are attached to an actual object, the relevant position may not be found.

Meanwhile, according to an embodiment of the present invention, the optimal stimulation position information (300, 310) provided on the coordinate system of the derived 10-20 system may be guided through a standardized coordinate system as illustrated in FIG. 10. Accordingly, medical staffs may easily detect the optimal stimulation position (300, 310) guided through the coordinate system of the 10-20 system. In addition, even if the electrodes are attached to an actual object, the exact optimal stimulation position (300, 310) may be found such that the brain stimulation operation is performed.

As described above, according to the present invention, even if objects (that is, individual patients) have different brain structures and head shapes, a medical image is acquired with respect to each object, and a 10-20 system is derived with respect to the object based on the medical image. Therefore, since the 10-20 system according to the present invention provides coordinate information obtained by reflecting different brain structures and head shapes of individual patients, more exact electrode position information may be provided with respect to each individual patient. In addition, since the medical staff may detect exact electrode position information through the 10-20 system, an operation effect may be improved for a relevant patient, when a brain stimulation operation is performed with respect to the relevant patient. In addition, medical staffs may receive the standardized position information when obtaining a position, to which an electrical stimulation is applied, on the head of the object by using the 10-20 system, and may visually easily detect the position information.

In addition, as described above, according to the present invention, when the position of the optimal stimulation applied to the head of the target is calculated by using the 10-20 system, the computation amount may be reduced to rapidly obtain the result. In addition, as the optimal stimulation position is marked on the coordinate system of the 10-20 system, the medical staffs may effectively detect the relevant position and may attach an electrode to an exact position. Accordingly, the operation effect may be improved.

Figure 11:
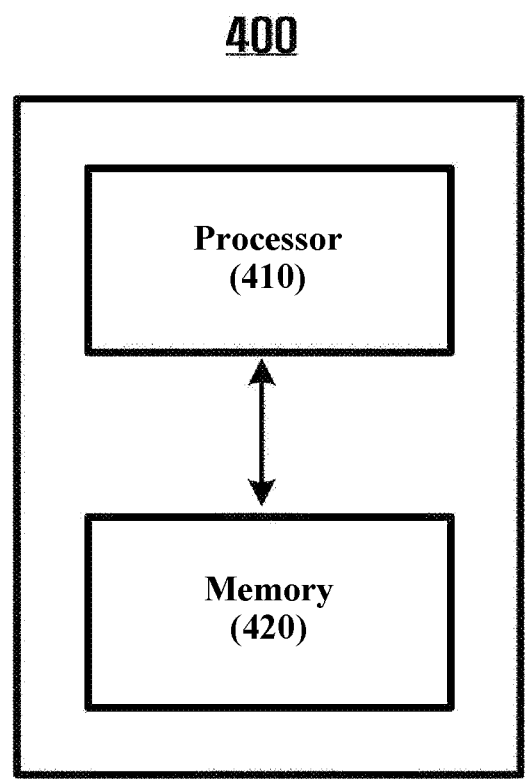
FIG. 11 is a view schematically illustrating a device for performing a method for providing position information based on a 10-20 system, according to an embodiment of the present invention.

FIG. 11 is a view schematically illustrating a device 400 for performing a method for providing position information based on a 10-20 system, according to an embodiment of the present invention.

Referring to FIG. 11, a processor 410 may include at least one core (not illustrated), a graphic processing unit (not illustrated), and/or a connection passage (for example, a bus) to transmit or receive a signal together with another component.

According to an embodiment, the processor 410 performs the method for providing position information based on the 10-20 system described with reference to FIGS. 1 to 10, by executing at least one instruction stored in a memory 420.

For example, the processor 410 may execute the at least one instruction stored in the memory 420 to acquire a head image of an object, receive at least four reference points based on the head image from a user, calculate central coordinates of the head image based on the at least four reference points, and provide position information based on the 10-20 system based on the central coordinates.

Meanwhile, the processor 410 may further include a random access memory (RAM; not illustrated) and a read-only memory (not illustrated) to temporarily and/or permanently store a signal (or data) processed in the processor 410. In addition, the processor 410 may be implemented in the form of a system on chip (SoC) including at least one of a graphic processing unit, a RAM, and a ROM.

The memory 420 may store programs (one or more instructions) for processing and controlling by the processor 410. The programs stored in the memory 420 may be partitioned into a plurality of modules depending on functions.

As described above, according to an embodiment of the present invention, the method for providing the position information based on the 10-20 system may be implemented in the form of a program (or application) which is linked to a computer, which is hardware, and executed and stored in a medium.

The method or the algorithm steps described regarding the embodiment of the present invention may be implemented in hardware, and implemented with a software module executed by the hardware, or the combination of the software and the hardware. A software module may reside in a random access memory (RAM), a read only memory (ROM), an erasable programmable ROM (EPROM), an electrically erasable programmable ROM (EEPROM), a flash memory, a hard disk, a removable disk, a CD-ROM, or a computer readable recording medium well known in the art to which the present invention pertains.

According to the present invention, the medical image of each object may be acquired and the 10-20 system may be derived with respect to the object, based on the medial image. Accordingly, coordinate information obtained by reflecting different brain structures and head shapes of individual patients may be provided with respect to the individual patients. In addition, the exact electrode position information may be provided for each of the individual patients through the 10-20 system. Accordingly, the operation effect may be improved when the brain stimulation operation is performed. In addition, the standardized position information may be provided by using the 10-20 system, and the position for an electrode may be visually easily detected.

According to the present invention, when the optimal stimulation position is calculated by using the 10-20 system, the computation amount may be more reduced as compared to a conventional manner. In addition, the optimal stimulation position is marked on the coordinate system of the 10-20 system, such that the medial staffs may effectively detect the relevant position and may attach the electrode to the exact position.

The effects of the present invention are not limited to the above, but other effects, which are not mentioned, will be apparently understood to those skilled in the art.

While the present invention has been described with reference to exemplary embodiments, it will be apparent to those skilled in the art that various changes and modifications may be made without departing from the spirit and scope of the present invention. Therefore, it should be understood that the above embodiments are not limiting, but illustrative.

What is claimed is:

1. A method for providing position information based on a 10-20 system, which is performed by a device, the method comprising:
    obtaining a head image of an object;
    receiving, from a user, at least four reference points based on the head image, by receiving front, back, left, and right reference points of a head, which are included in the head image;
    calculating central coordinates of the head image, based on the at least four reference points;
    providing the position information based on the 10-20 system, based on the central coordinates; and
    deriving a coordinate system of the 10-20 system by using distance information on a first connection line, which is obtained by linking the front reference point of the head to the back reference point of the head based on the central coordinates, and distance information on a second connection line which is obtained by linking the left reference point of the head to the right reference point of the head based on the central coordinates.

2. The method of claim 1, wherein the calculating of the central coordinates of the head image includes:
    calculating a point, at which the front, back, left, or right reference points of the head cross each other, as the central coordinates.

3. The method of claim 1, further comprising:
    setting a position of an electrode, which is to be attached to the head of the object, on the head image,
    wherein the providing of the position information based on the 10-20 system includes:
    providing information on the set position of the electrode based on the central coordinates of the 10-20 system; and
    calculating the position information of the electrode based on a first point extending from a point, at which the electrode is positioned, and positioned on the first connection line or a second point extending from the point, at which the electrode is positioned, and positioned on the second connection line.

4. The method of claim 3, wherein the calculating of the position information of the electrode includes:
    deriving a first distance of the electrode, based on a geodesic line between the central coordinates and the first point;

deriving a second distance of the electrode, based on a geodesic line between the first point and the point at which the electrode is positioned; and calculating the position information of the electrode on a coordinate system of the 10-20 system, based on the first distance of the electrode and the second distance of the electrode.

5. The method of claim 3, wherein the calculating of the position information of the electrode includes:

deriving a first distance of the electrode, based on a geodesic line between the central coordinates and the second point;

deriving a second distance of the electrode, based on a geodesic line between the second point and the point at which the electrode is positioned; and calculating the position information of the electrode on a coordinate system of the 10-20 system, based on the first distance of the electrode and the second distance of the electrode.

6. The method of claim 1, further comprising:

providing information on an optimal stimulation position, to which an electrical stimulation is applied, of a head of the object, based on the position information based on the 10-20 system.

7. A non-transitory recording medium which is computer-readable and has a computer program to operate a computer to perform the method for providing the position information based on the 10-20 system, according to claim 1.

8. A method for providing position information based on a 10-20 system, which is performed by a device, the method comprising:

obtaining a head image of an object;

receiving, from a user, at least four reference points based on the head image;

calculating central coordinates of the head image, based on the at least four reference points;

providing the position information based on the 10-20 system, based on the central coordinates; and providing information on an optimal stimulation position, to which an electrical stimulation is applied, of a head of the object, based on the position information based on the 10-20 system, wherein the providing of the information on the optimal stimulation position includes:

simulating stimulation results for a plurality of stimulation positions, based on the plurality of stimulation positions provided by the 10-20 system;

deriving a linear relationship between the plurality of stimulation positions by using the simulated stimulation results; and providing the information on the optimal stimulation position based on the linear relationship.

9. The method of claim 8, wherein the simulating of the stimulation results for the plurality of stimulation positions includes:

setting one reference stimulation position of the plurality of stimulation positions; and acquiring a stimulation result for a stimulation pair between the reference stimulation position and each of different stimulation positions of the plurality of stimulation positions other than the reference stimulation position.

10. The method of claim 9, wherein the deriving of the linear relationship between the plurality of stimulation positions includes:

driving a linear relationship between electric fields, which are output, as a specific stimulation is applied under a specific stimulation condition, from the stimulation result for the stimulation pair.

11. The method of claim 10, wherein the providing of the information on the optimal stimulation position includes:

providing the information on the optimal stimulation position under a desired stimulation condition, based on the linear relationship.

12. A device for providing position information based on a 10-20 system, the device comprising:

a memory configured to store at least one instruction to provide the position information based on the 10-20 system; and a processor configured to execute the at least one instruction stored in the memory, wherein the processor is configured to:

obtain a head image of an object;

receive, from a user, at least four reference points including front, back, left, and right reference points of a head, which are included in the head image;

calculate central coordinates of the head image, based on the at least four reference points, provide the position information based on the 10-20 system, based on the central coordinates, in response to at least one instruction which is executed, when the at least one instruction is executed; and derive a coordinate system of the 10-20 system by using distance information on a first connection line, which is obtained by linking the front reference point of the head to the back reference point of the head based on the central coordinates, and distance information on a second connection line which is obtained by linking the left reference point of the head to the right reference point of the head based on the central coordinates.

13. The device of claim 12, wherein the processor is configured to:

calculate a point, at which the front, back, left, or right reference points of the head cross each other, as the central coordinates, when calculating the central coordinates on the head image.

* * * * *